(12) United States Patent
Polsky et al.

(10) Patent No.: US 7,442,507 B2
(45) Date of Patent: Oct. 28, 2008

(54) METHODS FOR DETECTING CIRCULATING MUTANT BRAF DNA

(75) Inventors: David Polsky, Ardsley, NY (US); Iman Osman, Port Liberte, NJ (US); Paul B. Chapman, New York, NY (US)

(73) Assignees: New York University School of Medicine, New York, NY (US); Memorial Sloan-Kettering Cancer Center, New York, NY (US)

( * ) Notice: Subject to any disclaimer, the term of this patent is extended or adjusted under 35 U.S.C. 154(b) by 305 days.

(21) Appl. No.: 11/338,615

(22) Filed: Jan. 24, 2006

(65) Prior Publication Data

US 2006/0246476 A1      Nov. 2, 2006

Related U.S. Application Data

(60) Provisional application No. 60/646,699, filed on Jan. 24, 2005.

(51) Int. Cl.
*C12Q 1/68* (2006.01)

(52) U.S. Cl. .................. 435/6; 435/91.1; 435/91.2

(58) Field of Classification Search ............ None
See application file for complete search history.

(56) References Cited

OTHER PUBLICATIONS

Xu et al., High Prevalence of BRAF Gene Mutation in Papiliary Thyroid Carcinomas and Thyroid Tumor Cell Lines, Cancer Research, 63:4561-4567 (2003).
Iinuma et al., Detection of Tumor Cells in Blood Using CD45 Magnetic Cell Separation Followed By Nested Mutant Allele-Specific Amplification of *p53* and K-*ras* Genes in Patients Colorectal Cancer, Int. J. Cancer (Pred. Oncol.), 89:337-344 (2000).
C. Esche, First Study on BRAF Mutation In the Serum of Melanoma Patients, 553, vol. 122, No. 3, Mar. 2004 (Abstract).
Yancovitz et al., Detection of Mutant *BRAF* Alleles In The Plasma of Patients With Metastatic Melanoma, Journal of Molecular Diagnostics, 9:178-183 (2007).
Kondo et al., Detection of Point Mutations in the K-*ras* Oncogene at Codon 12 in Pure Pancreatic Juice For Diagnosis of Pancreatic Carcinoma, Cancer, 73:1589-1594 (1994).
Pellegata et al., K-*ras p53* Mutations in Pancreatic Cancer: Ductal and Nonductal Tumors Progress through Different Genetic Lesions, Cancer Research, 54:1556-1560 (1994).
Yamada et al., Detection of K-*ras* Gene Mutations in Plasma DNA of Patients with Pancreatic Adenocarcinoma: Correlation with Clinicopathological Features, Clinical Cancer Research, 4:1527-1532 (1998).
Kopreski et al., Detection of mutant K-*ras* DNA in plasma or serum of patients with colorectal cancer, British Journal of Cancer, 76:1293-1299 (1997).
Miller et al., The Journal of Investigative Dermatology, 123:990-992 (2004).

*Primary Examiner*—Gary Benzion
*Assistant Examiner*—Heather G. Calamita
(74) *Attorney, Agent, or Firm*—Klauber & Jackson LLC

(57) ABSTRACT

The present invention relates to a method for detecting the presence of circulating mutant BRAF DNA, which may be present in circulating melanoma cells or as DNA shed from tumor cells. Methods, compositions and kits which employ one or more sets of BRAF mutant specific primer pairs for detection of circulating mutant BRAF DNA are presented. Also provided are methods for diagnosing and/or determining stage/progression of a melanoma in a mammal based on detection of a BRAF mutant nucleic acid sequence. Such methods are also well suited to monitoring disease activity in patients with active disease or those in remission.

20 Claims, 10 Drawing Sheets

BRAF Exon 15 Sequence (Reverse Complement)

```
5'
tttttattc  ttgtgactaa  aaacacttat  gacccttgat  acttttatga  tatcaactct
aaaaaataag  aacactgatt  tttgtgaata  ctgggaacta  tgaaaatact  atagttgaga
3' ggaagttact  gaaagatcat  tgagtcgtcg  tagagtcccg  gttttaaat  tagtcacctt ccttcaatga  ctttctagta  actcagcagc  atctcag ggc  caaaaattta  atcagtggaa
                                         ─────────────────────────► tttatcggag  ttaagaatgg  taggagtttt  acctaggtct  gttgacaagt  ttgactaccc aaatagcctc  aattcttacc  atccacaaaa  tggatccaga  caactgttca  aactgatggg
                                                                 ■
                                                                 G
    AGGT AGCTCTAAAG  AGACATCGA
  ◄─────────────────────────
              ATACATCGAT CTGGTTTTAG TGG
            ◄────────────────────────
tgggtgaggt  agctctaaag  tgacatcgat  ctggttttag  tggataaaaa  tgacactcca acccactcca  tcgagatttc  actgtagcta  gaccaaaatc  acctattttt  actgtgaggt
              AGATTTC TCTGTAGCTA GACCAAAA
            ──────────────────────────►
       A TCGAGATTTC TCTGTAGCT
       ──────────────────────►
ACCCACTCCA TCGAGATTTA T
─────────────────────► gaagtacttc  tttatataga  ctccacatca  ttcatttcct  tttgtcatct  agagtaaaag
                                                                    ◄
cttcatgaag  aaatatatct  gaggtgtagt  aagtaaagga  aaacagtaga  tctcattttc 3'
gatagtctcg  ttcgtaatac  ttctcaaatc  cattctctag  attaaagata  ttaagacatt ctatcagagc  aagcattatg  aagagtttag  gtaagagatc  taatttctat  aattctgtaa
                                                                 5'
```

LEGEND:

◄── BRAF 15 WT FORWARD (sequence in blue)     ──► BRAF 15 WT REVERSE (sequence in black)

◄─── BRAF 15 Mutant Specific FR-1     ──► BRAF 15 Mutant Specific R-1
*works with WT reverse primer ◄── BRAF 15 Mutant Specific FR-2     ═══► BRAF 15 Mutant Specific R-2
*works with modified WT reverse primer (──►)     ──► BRAF 15 Mutant Specific R-3
                                         *all reverse primers work with WT forward primer

FIG. 1A

FIG. 9A
FIG. 9B
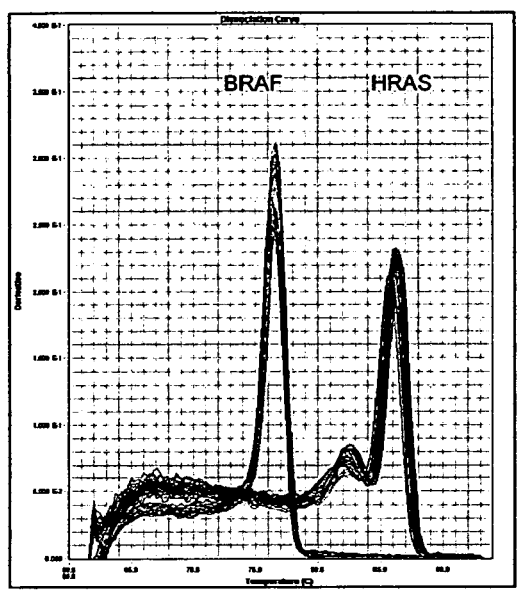
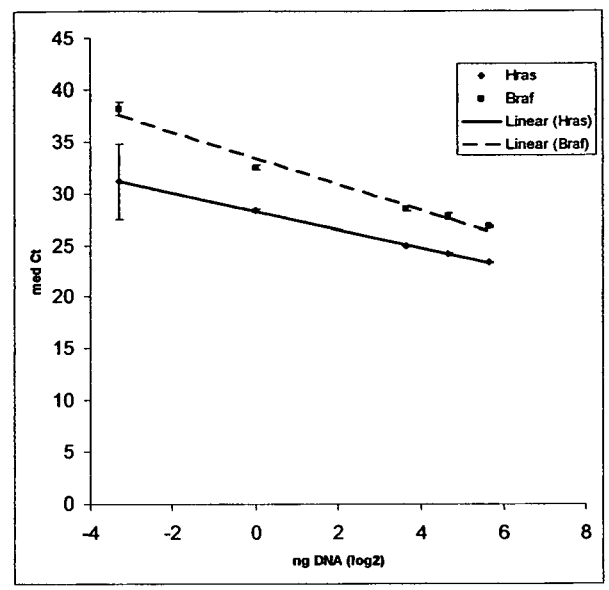

METHODS FOR DETECTING CIRCULATING MUTANT BRAF DNA

CROSS REFERENCE TO RELATED APPLICATIONS

This application claims priority under 35 U.S.C. § 119(e) to U.S. Provisional Application No. 60/646,699 filed Jan. 24, 2005, which application and the entire disclosure thereof is herein specifically incorporated by reference in its entirety.

FIELD OF THE INVENTION

The present invention relates to a method for detecting the presence of circulating mutant BRAF DNA in peripheral blood. Such circulating mutant BRAF DNA may be present in circulating melanoma cells or as DNA shed from tumor cells. Accordingly, the method of the present invention may be used to advantage for diagnosing and/or staging melanoma. Such a method is also useful for applications directed to determining the efficacy of a melanoma treatment regimen and/or monitoring the status of a patient in remission.

BACKGROUND OF THE INVENTION

Several publications and patent documents are referenced in this application in order to more fully describe the state of the art to which this invention pertains. The disclosure of each of these publications and documents is incorporated by reference herein in its entirety.

Exciting progress has been made in melanoma biology. In the last several years a model of human melanocyte transformation has emerged based on the combined results of human genetic studies, cell biology, molecular pathology and mouse modeling (Chin. Nat Rev Cancer 2003; 3:559-70). Initial studies that identified the autocrine production of basic fibroblast growth factor as an early event in melanocyte transformation have been augmented by recent studies identifying ERK activation in melanoma tissues (Cohen et al. Clin Cancer Res 2002; 8:3728-33) and cell lines (Satyamoorthy et al. Cancer Res 2003; 63:756-9), and most importantly by the discovery of frequent BRAF mutations in melanoma tissues (Gorden et al. Cancer Res 2003; 63:3955-7; Davies et al. Nature 2002; 417:949-54; Dong et al. Cancer Res 2003; 63:3883-5; Kumar et al. Clin Cancer Res 2003; 9:3362-8; Pollock et al. Nat Genet 2003; 33:19-20; Uribe et al. Am J Dermatopathol 2003; 25:365-70; Yazdi et al. Pigment Cell Res 2003; 16:580). Many melanomas possessing mutant BRAF alleles have also acquired extra copies of the these alleles (Maldonado et al. J Natl Cancer Inst 2003; 95:1878-90). BRAF acts downstream of RAS, and studies have demonstrated that simultaneous mutations in RAS and BRAF are extremely rare in melanoma (Gorden et al. 2003, supra; Davies et al. 2002, supra; Dong et al. 2003, supra; Kumar et al. 2003, supra; Pollock et al. 2003, supra), suggesting that BRAF mutations substitute for at least some of the oncogenic function of mutant RAS. Experimental studies have demonstrated that several BRAF mutations, especially the V600E hotspot mutation (which was originally designated V599E, but has been renumbered V600E in accordance with advances in the field; see Kumar et al. 2003 supra), which accounts for 90% of BRAF mutations in melanoma, activate the MAPK cascade and can transform fibroblasts in culture (Davies et al. 2002, supra; Dong et al. 2003, supra).

In the clinic the treatment of metastatic melanoma remains one of the most formidable challenges today. Survival is best predicted by tumor stage, with patients with distant metastases (Stage IV) having a median survival of only 6 to 9 months, and 5-year survival rates of only 1% to 5%. Five-year survival of patients with regional lymph node disease (Stage III) ranges from 13% to 69% depending upon the number of nodes involved, the volume of disease in the nodes (microscopic only vs. clinically palpable) and thickness and ulceration status of the primary tumor. In clinically localized, stage I/II disease, 5-year survival ranges from 45% to 95% depending upon tumor thickness and the presence of ulceration (Balch et al. J Clin Oncol 2001; 19:3622-34). Patients whose tumors are thicker than 1 mm are often referred for sentinel lymph node biopsy. This technique aims to detect microscopic lymph node involvement, thereby selecting patients who might benefit from a regional lymph node dissection. However, the benefit of regional lymph node dissection is still debated among oncologists, as patients eventually succumb to melanoma due to the hematogenous dissemination of tumor cells (Balch et al. Elective Lymph Node Dissection. In: Balch CM, Houghton A, Sober A, Soong R, eds. Cutaneous Melanoma. St. Louis: Quality Medical, 2003:379-395).

The development of tumor markers to better stratify patients for their risk of developing metastases is under active investigation. Although assessment of tumor markers and selection of treatment based on the results has been part of the standard of care in colon and breast cancer management for several years (Bast et al. J Clin Oncol 2001; 19:1865-78), no such markers exist for melanoma. Several papers have been published investigating growth control genes, extracellular matrix-degrading enzymes, adhesion/signaling molecules, angiogenic factors and immunoregulatory molecules (Hwu et al. Diagnosis of Stage IV Disease. In: Balch CM, Houghton A, Sober A, Soong S, eds. Cutaneous Melanoma. St. Louis: Quality Medical, 2003:523-546 and references therein). Many studies have shown promise, but none have moved past the preliminary stages of development into a clinically useful assay. Most of these studies are based on immunohistochemistry, and it is anticipated that inter-laboratory variability will be a major obstacle to the adoption of all but the most promising markers (McShane et al. Clin Cancer Res 2000; 6:1854-64). Moreover, techniques involving immunohistochemistry are not well suited to rapid screening approaches because they are time consuming, and require invasive procedures for sample isolation and a significant degree of technical expertise.

In view of the above, new methods for use in the accurate diagnosis, prognosis, and/or monitoring of patients with melanoma are urgently needed. The method of the present invention addresses this need.

SUMMARY

The present invention is directed to a novel method for detecting circulating mutant BRAF DNA in the peripheral blood of patients. Circulating mutant BRAF DNA may be present in circulating melanoma cells or as DNA shed from tumor cells. Detection of mutant BRAF DNA in the peripheral blood serves as a positive indicator of metastatic melanoma. As such, the present method serves as a useful indicator and/or predictor of outcome for melanoma patients. Accordingly, results generated using the present method provide guidance with regard to therapeutic regimens appropriate for a melanoma patient. The present method may also be used to determine the mutation status of BRAF in a patient's tumor without requiring that the patient undergo the pain and potential complications associated with biopsy procedures. Knowledge of the BRAF mutation status of a tumor is an important consideration when determining if treatment with BRAF inhibitors or other related compounds under development is merited.

In an aspect of the invention, a method for diagnosing metastatic melanoma in a subject is described which comprises:

(a) isolating a fluid sample from the subject, wherein the fluid sample comprises nucleic acid sequences;

(b) performing an amplification reaction of the nucleic acid sequences of the sample, wherein the amplification reaction comprises a first primer capable of annealing specifically to a BRAF mutant sequence at a first position in a BRAF nucleic acid sequence and a second primer capable of annealing specifically at a second position in a BRAF nucleic acid sequence, wherein the first and second primers anneal to different strands of double stranded BRAF nucleic acid sequence, wherein the amplification reaction is capable of producing a BRAF mutant specific amplification product when the nucleic acid sequences of the sample comprise a BRAF nucleic acid sequence comprising a mutant sequence at the first position of said BRAF nucleic acid sequence; and (c) visualizing amplification products produced by the amplification reaction, wherein detection of a BRAF mutant specific amplification product is a positive indicator of metastatic melanoma in the subject.

In another aspect of the invention, the present method is used to detect metastatic melanoma in a subject before disease is clinically apparent, wherein detection of a BRAF mutant specific amplification product is a positive indicator of metastatic melanoma in the subject.

In another aspect of the invention, the present method is used for determining the efficacy of a treatment in a subject afflicted with metastatic melanoma, wherein detection of a BRAF mutant specific amplification product or increased levels of BRAF mutant specific amplification product is a positive indicator of reduced efficacy of the treatment in the subject afflicted with metastatic melanoma.

In another aspect of the invention, the present method is of utility for predicting clinical benefit of or determining continued clinical benefit from administering a cancer intervention regimen to a subject, wherein detection of BRAF mutant specific amplification product levels is indicative that administering the cancer intervention regimen to the subject is capable of effectuating clinical benefit in the subject or continues to effect clinical benefit to the subject. In one embodiment of the invention, the cancer intervention regimen comprises administering agents capable of inhibiting BRAF activity or a Ras-Raf-MAPK cascade. Clinical benefit is measurable, for example, as a decrease in tumor burden (e.g., number of circulating metastatic melanoma cells or reduction in primary tumor mass), a reduction in symptoms associated with the disease, and/or achievement of remission from disease. The method may also be used to advantage to monitor disease remission in a subject following a cancer intervention regimen. The present method may be used to monitor/evaluate previously treated subjects to detect the reappearance of cancer/relapse or reaffirm disease remission.

In one embodiment, the sample is peripheral blood. Peripheral blood samples may be further processed to remove erythrocytes, thereby producing a population of erythrocyte-depleted peripheral blood cells. Nucleic acid sequences may be isolated from, for example, either total peripheral blood or erythrocyte-depleted peripheral blood cells, including buffy coat preparations. The method of the invention may also be used to detect "free" nucleic acid sequences (or nucleic acid sequences that are not associated with intact cells) in plasma (the liquid phase of blood) or serum (the liquid that remains after blood has clotted). Of note in this regard, cancer patients generally have higher levels of circulating free nucleic acid sequences.

In an aspect of the present method, the BRAF mutant sequence at a first position in a BRAF nucleic acid sequence comprises a T1799A mutation (formerly numbered T1796A) in BRAF exon 15. Exemplary primers capable of annealing specifically to a BRAF mutant sequence at this first position in a BRAF nucleic acid sequence include SEQ ID NO: 1; SEQ ID NO: 2; SEQ ID NO: 3; SEQ ID NO: 6; and SEQ ID NO: 7. BRAF mutant specific amplification products indicative of metastatic melanoma range in size from approximately 128 base pairs using BRAF mutant specific primer pair SEQ ID NO: 1 and SEQ ID NO: 4; to approximately 132 base pairs using BRAF mutant specific primer pair SEQ ID NO: 2 and SEQ ID NO: 4; to approximately 112 base pairs using BRAF mutant specific primer pair SEQ ID NO: 3 and SEQ ID NO: 5; to approximately 125 base pairs using BRAF mutant specific primer pair SEQ ID NO: 5 and SEQ ID NO: 6; to approximately 140 base pairs using BRAF mutant specific primer pair SEQ ID NO: 4 and SEQ ID NO: 7.

The present method is compatible with nested polymerase chain reaction (PCR) amplifications. Accordingly, in one embodiment, the present method further comprises a preliminary amplification reaction of the nucleic acid sequences of the sample performed prior to the amplification reaction of step (b). A preliminary amplification reaction comprises first and second primers capable of annealing specifically to a BRAF nucleic acid sequence, wherein the first and second primers anneal to different strands of double stranded BRAF nucleic acid sequence and the preliminary amplification reaction produces a BRAF amplification product capable of amplification using said first and second primers of step (b).

To enhance the sensitivity of the method, at least one of the first or second primers of step (b) may be fluorescently labeled and amplification products produced by amplification reactions using such labeled primers are also fluorescently labeled. Fluorescently labeled BRAF mutant specific amplification products may be visualized by a variety of means known in the art as described herein.

Also encompassed by the present invention are novel BRAF mutant specific primers. Exemplary BRAF mutant specific primers include nucleic acid sequences comprising one of a nucleic acid sequence of SEQ ID NO: 1; SEQ ID NO: 2; SEQ ID NO: 3; SEQ ID NO: 6; or SEQ ID NO: 7. As described herein, such primers can be fluorescently labeled.

BRAF mutant specific primers (SEQ ID NO: 1; SEQ ID NO: 2; SEQ ID NO: 3; SEQ ID NO: 6; or SEQ ID NO: 7) or appropriate BRAF mutant specific primer pairs (SEQ ID NO: 1 and SEQ ID NO: 4; SEQ ID NO: 2 and SEQ ID NO: 4; SEQ ID NO: 3 and SEQ ID NO: 5; SEQ ID NO: 5 and SEQ ID NO: 6; or SEQ ID NO: 4 and SEQ ID NO: 7) may be components of compositions comprising biologically compatible salt solutions.

The present invention also includes a kit for detecting metastatic melanoma in a mammal which comprises:

a) a container for storing a biological sample obtained from the mammal;

b) a composition comprising at least one BRAF mutant specific primer pair in an amount effective to permit detection of BRAF mutant nucleic acid sequence, if present, in said sample and a biologically compatible salt solution;

c) positive and negative control nucleic acid sequences of the BRAF exon 15 sequence; and d) an instructional material setting forth a protocol suitable for use in detecting and/or quantifying BRAF mutant nucleic acid sequences.

In another aspect of the present invention, a method for detecting BRAF mutant status in a subject is described. The method comprises:

(a) isolating a sample from said subject, wherein said sample is a tumor sample or a fluid sample and comprises nucleic acid sequences;

(b) performing an amplification reaction of said nucleic acid sequences of said sample, wherein said amplification reaction comprises a BRAF mutant specific primer pair; wherein said amplification reaction is capable of producing a BRAF mutant specific amplification product when said nucleic acid sequences of said sample comprise a mutant BRAF nucleic acid sequence comprising a mutant sequence to which one primer of the BRAF mutant specific primer pair specifically anneals; and (c) visualizing amplification products produced by said amplification reaction, wherein detection of a BRAF mutant specific amplification product indicates that a BRAF mutant allele is present in said subject.

In one embodiment of this aspect of the invention, the BRAF mutant specific primer pair is SEQ ID NO: 1 and SEQ ID NO: 4. In a different embodiment, the BRAF mutant specific primer pair is SEQ ID NO: 2 and SEQ ID NO: 4. In an alternate embodiment, the BRAF mutant specific primer pair is SEQ ID NO: 5 and SEQ ID NO: 3. In another embodiment, the BRAF mutant specific primer pair is SEQ ID NO: 5 and SEQ ID NO: 6. In yet another embodiment, the BRAF mutant specific primer pair is SEQ ID NO: 7 and SEQ ID NO: 4.

BRIEF DESCRIPTION OF THE DRAWINGS

FIGS. 9A and B show (A) dissociation curves for BRAF and HRAS (sharp peaks demonstrate the specificity of the primers) and (B) standard curves of BRAF and HRAS.

DEFINITIONS

Figure 1B:
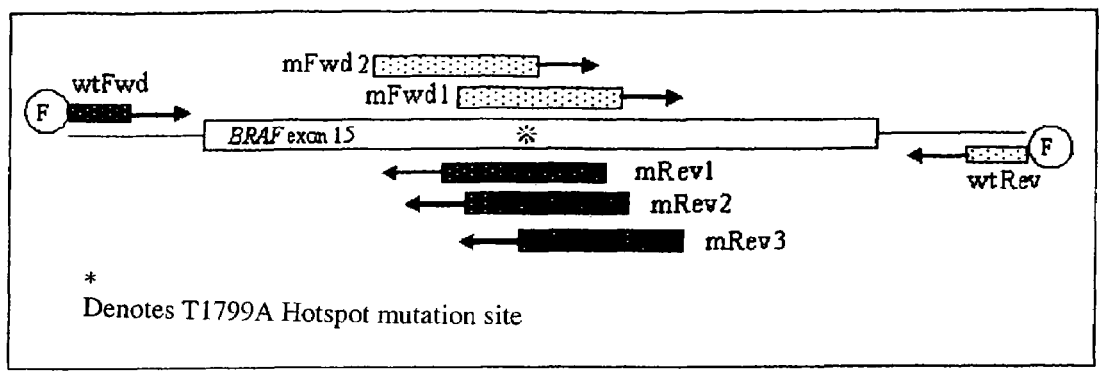
FIGS. 1A and B show a nucleic acid sequence of BRAF exon 15 (SEQ ID NO: 8) that depicts the sites at which the indicated primers anneal (A) and a diagram depicting BRAF exon 15 flanked by intronic sequences (thin lines) and an alignment of several of the BRAF specific PCR primers described herein (B).

Various terms relating to the molecules and methods of the present invention are used hereinabove and also throughout the specifications and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

A "vector" is a replicon, such as plasmid, phage, cosmid, or virus into which another nucleic acid segment may be operably inserted so as to bring about the replication or expression of the segment.

An "expression vector" is a vector which (due to the presence of appropriate transcriptional and/or translational control sequences) is capable of expressing a DNA molecule which has been cloned into the vector and of thereby producing an RNA or protein product encoded by an expressible gene provided by said DNA. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, e.g., for genetic manipulation prior to gene delivery, then the appropriate host cell would be any eukaryotic cell capable of expressing the cloned sequences.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. In other applications, the introduced nucleic acid may exist in the recipient cell or host organism only transiently.

The term "substantially pure" refers to a preparation comprising at least 50-60% by weight of the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide or amino acid means a sequence having the properties of a given SEQ ID NO:. For example, when used in reference to an amino or nucleic acid sequence, the phrase includes the sequence per se and molecular modifications that would not affect the basic and novel characteristics of the sequence. With regard to the novel primers of the present invention, for example, the phrase includes the sequence per se and molecular modifications that would not appreciably affect the ability of the primer to act as a BRAF mutant specific primer.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nlm.nih.gov/blast/; Altschul et al., 1990, J Mol Biol 215:403-410) using a gapped alignment with default parameters, may be used to determine the level of identity and homology between nucleic acid sequences and amino acid sequences.

With respect to single stranded nucleic acids, particularly oligonucleotides, the terms "specifically hybridizing" or "specifically annealing" refer to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. Preferred oligonucleotides comprise 15-50 consecutive bases of SEQ ID NO: 8 (BRAF exon 15 sequence). Exemplary BRAF mutant-specific PCR primers of the present invention are nucleic acid sequences comprising one of SEQ ID NOs: 1-3, 6, or 7. The present invention also encompasses BRAF mutant-specific PCR primers which share at least about 80% homology with nucleic acids of any one of SEQ ID NO: 1-3, 6, or 7.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "functional" as used herein implies that the nucleic or amino acid sequence is functional for the recited assay or purpose.

The term "melanoma" as used herein may be used to refer to either primary melanoma or metastatic melanoma.

The term "BRAF mutant specific amplification product" as used herein refers to a product generated by an amplification reaction from a mutant BRAF nucleic acid sequence comprising a mutation at a specific position in the BRAF nucleic acid sequence.

The term "biologically compatible salt solution" is used herein to describe any salt solution in which nucleic acid sequences may be stably maintained. For applications wherein nucleic acid sequences in such salt solutions are to be amplified, such salt solutions are modifiable (e.g., capable of being diluted or altered to change substituent concentration) to be compatible with polymerase activity and the like.

DETAILED DESCRIPTION OF THE INVENTION

Despite recent advances in the study of melanoma biology, the development of molecular tools useful for diagnosing and/or monitoring patients with melanoma is still embryonic. Few advances have been made in protocols designed to monitor patients for disease recurrence, or to select patients at high risk for the development of metastases. Tumor stage, the best predictor of survival from melanoma, is based on conventional clinicopathologic variables such as thickness and ulceration of the primary tumor, and the presence of metastatic disease in regional lymph nodes or at distant sites. Two patients with primary tumors of intermediate thickness (1.0-4.0 mm thick) that appear microscopically identical can, however, have dramatically different survivals. The absence of improved prognostic tools for such assessments makes it difficult for attending physicians to determine the best treatment strategies.

Recently, mutations in the BRAF oncogene have been discovered in up to 80% of melanoma tissues, frequencies strikingly higher than any other molecular alteration in this disease. BRAF mutations have also been detected in tumor tissues from other types of cancer. Experimental studies have demonstrated that several BRAF mutations, especially the T1799A (formerly designated T1796A) hotspot mutation, which accounts for 90% of BRAF mutations in melanoma, can transform fibroblasts in culture. Most recently, experiments blocking the expression of mutant BRAF in melanoma cell culture were shown to inhibit cell growth and promote cell death, suggesting that BRAF inhibitors could bolster melanoma treatment significantly (Hingorani et al. 2003, supra).

As described herein, the present inventors have developed a novel method for detecting the presence of mutant BRAF DNA in the peripheral blood of patients. Accordingly, the present method may be used advantageously to diagnose melanoma in a subject, detect metastasis of a primary melanoma in a subject, and/or assess the therapeutic efficacy of a drug or compound administered to treat a subject with melanoma. The method is directed to a PCR amplification strategy that specifically amplifies the T1799A BRAF mutant that has been implicated in melanoma. The method utilizes novel oligonucleotide primers (mRev1, SEQ ID NO: 1; mRev2, SEQ ID NO: 2; mFwd1, SEQ ID NO: 3; mFR-2, SEQ ID NO: 6; and mR3, SEQ ID NO: 7) that specifically amplify alleles comprising the T1799A hotspot mutation of BRAF, as determined in polymerase chain reaction (PCR) amplifications. A diagram depicting the general amplification strategy is shown in FIGS. 1A and 1B.

The mutant-specific PCR approach exemplified herein is also well applied to other genes that have sustained point mutations in specific codons (e.g. RAS, MITF, others) that are associated with melanoma. Applying these assays in combination would enhance the sensitivity of such tests for the presence of melanoma in a patient. For example, it is known that the presence of mutations in BRAF and NRAS is mutually exclusive. Assays designed to detect either mutant gene would, therefore, be more sensitive than assays designed to detect only one. In addition, genes that have sustained point mutations are important targets for therapeutic interventions. Applying this approach to the detection of other mutated genes will facilitate the identification of patients eligible for specific therapeutic regimens, and the monitoring of their responses to such regimens.

Inasmuch as the present method is performed on a biological sample isolated from a subject (e.g., a human patient) and is capable of detecting mutant BRAF DNA in, for example, a peripheral blood isolate from such a subject, the method can be performed on a routine basis. It is noteworthy that prior to the discovery of the present inventors, there was no reliable means of detecting mutant BRAF DNA in the peripheral blood of patients. In addition, there was no way to determine if a patient's tumor possesses mutant BRAF genes without obtaining a biopsy specimen. Knowledge of the BRAF mutation status of the tumor is an important factor for consideration when evaluating the potential benefits of treating a patient with BRAF inhibitors or other related compounds under development. One such anti-BRAF drug (BAY43-9006-NSC 724772) is currently the focus of Phase I studies to determine the appropriate dose for use in Phase II studies. Other agents known to inhibit the Ras-Raf-MAPK cascade, such as CI 1040, are suitable candidate drugs for administration to melanoma patients (Collisson et al. Cancer Res. 2003; 63:5669-5673). A rapid and accurate determination of BRAF mutation status, such as that obtainable using the present method, is of critical importance in a clinical assessment of those patients who would benefit from a therapeutic modality involving administration of BAY43-9006-NSC 724772, CI 1040, or other drug(s) with similar activity.

The invention is also useful as a predictor of outcome for melanoma patients. One of the key factors that contributes to improved outcome for a patient with any disease and in particular cancer, due to its progressive and invasive nature, is early and accurate diagnosis. The method of the present invention addresses the desperate need for a rapid, non-invasive, and accurate screening assay for detecting mutant BRAF DNA, the presence of which is a positive indicator of metastasizing disease. As such it identifies those patients who need to be treated with more aggressive treatment regimens. Moreover, since the invention detects DNA, sample preparation is facile, thereby reducing assay variability that can result from differences in the expertise level of laboratory technicians involved in sample preparation.

The method of the present invention may be used, for example, to monitor patients with advanced, metastatic melanoma (Stages III/IV). These patients are at the highest risk for disease progression, and early detection of an increase in disease activity would lead to earlier treatment and improvement in outcome. The method of the present invention may also be directed to testing patients with earlier stages of disease (Stages I/II), who are at risk for metastatic spread of their disease. Again, early intervention with additional diagnostic tests and treatments would lead to improved patient survival.

Although melanoma is described as an exemplary cancer for detection using the present method, a skilled artisan would appreciate that the method is equally well applied to any cancer associated or correlated with a BRAF mutation, such as that of the T1799A hotspot mutation of BRAF. Such cancers include, but are not limited to: melanoma, and cancers of the thyroid, ovary, colon, stomach, and pancreas, Barrettt's adenocarcinoma, pleural mesothelioma, non-Hodgkin's lymphoma, acute leukemia, squamous cell carcinoma of the head and neck, cholangiocarcinoma, and some subsets of lung adenocarcinoma.

The method comprises obtaining a sample of a tissue or a body fluid from the subject (e.g., a mammal). Non-limiting examples of tissue or body fluids that can be used include blood, plasma, lymph, and tumor biopsies.

The sample of the tissue or body fluid from the mammal or nucleic acid sequences isolated therefrom is contacted with a composition comprising a BRAF mutant-specific PCR primer pair and a biologically compatible salt solution. Exemplary BRAF mutant-specific PCR primers of the present invention are nucleic acid sequences comprising one of SEQ ID NOs: 1-3, 6, or 7. The present invention also encompasses BRAF mutant-specific PCR primers which share at least about 80% homology with nucleic acids of any one of SEQ ID NOs: 1-3, 6, or 7. BRAF mutant specific primer pairs include any combination of "forward" and "reverse" primer pairs capable of generating a BRAF mutant specific amplification product. Such BRAF mutant specific primer pairs include, for example: SEQ ID NO: 1 and SEQ ID NO: 4; SEQ ID NO: 2 and SEQ ID NO: 4; SEQ ID NO: 5 and SEQ ID NO: 3; SEQ ID NO: 5 and SEQ ID NO: 6; and SEQ ID NO: 7 and SEQ ID NO: 4. See Table 1 for additional details. PCR amplification of BRAF mutant nucleic acid sequences (template), if present in the sample, is performed using BRAF mutant specific primer pairs as described herein below.

To improve the sensitivity of the assay, one or both primers of a BRAF mutant specific primer pair used to amplify a BRAF mutant nucleic acid sequence may be fluorescently tagged or labeled. Primers may, for example, be labeled with 6'-FAM. PCR amplification products generated using such fluorescently labeled primers are, therefore, fluorescently labeled and detectable using equipment designed to detect fluorescent emissions. The ABI 310 Genetic Analyzer and Genescan 3.1.2 software (Applied Biosystems), for example, may be used for these analyses.

The sample can be contacted with the composition comprising at least one BRAF mutant specific PCR primer pair by any means routinely applied for contacting a sample with PCR primer pairs. For example, in one embodiment, the sample and the composition are contacted in a microwell plate or in a microvial adapted for the mixture of small volumes.

Sample Preparation from Primary Melanoma

Primary melanoma samples are generally preserved as formalin-embedded paraffin blocks. Tissue sections of varying thickness (~5 μm) are cut from such tissue blocks and mounted onto slides by standard means. The cellular morphology of the tissue sample is revealed using a variety of fixatives and/or stains and visualized microscopically at an appropriate magnification. If the density of melanoma cells in a tissue sample is sufficient (greater than about 1%), the section is scraped from the slide and DNA may be extracted directly from the total tissue sample without further purification of melanoma cells. Additional research has shown that the sensitivity of the assay is sufficient to detect ~1% density of melanoma cells, rather then 10% as originally estimated. The methodology for this procedure is described below:

DNA is isolated from clinical specimens using a modified version of the Qiagen QIAamp DNA Mini Kit.

DNA isolation from fresh and paraffin embedded tissues:
1. Up to 25 mg of fresh or frozen tissue are cut into small pieces and placed in a 2 uL microcentrifuge tube.
   *Formalin-fixed, paraffin embedded tissues require the following additional steps:
     a. Tumor tissue is macrodissected and scraped into a 1.5 mL microcentrifuge tube.
     b. To deparaffinize the tissue, 1200 uL of xylene are added and the sample is vortexed vigorously.
     c. The sample is centrifuged at full speed for 5 minutes.
     d. The supernatant is removed carefully by pipetting.
     e. 1200 uL of ethanol (96-100%) are added to the pellet to remove residual xylene and mixed gently by vortexing.
     f. The sample is centrifuged at full speed for 5 minutes at room temperature.
     g. Ethanol supernatant is removed carefully by pipetting.
     h. Steps e-g are repeated.
     i. The open microcentrifuge tube is incubated at 37° C. for 10-15 minutes until the ethanol has evaporated.
2. The tissue pellet is suspended in 180 uL Buffer ATL.
3. 20 uL Proteinase K are added, the sample is mixed by vortexing, and incubated at 56° until the tissue is completely lysed (usually >3 hours). During incubation, the sample is vortexed every 20 minutes to ensure the sample is dispersed.
4. The microcentrifuge tube is centrifuged to remove drops from the inside of the lid.
5. 200 uL of Buffer AL are added to the sample, mixed by pulse vortexing for 15 seconds, and incubated at 70° for 10 minutes. The microcentrifuge tube is centrifuged briefly to remove drops from inside the lid.
   *A white precipitate may form on addition of Buffer AL, which in most cases will dissolve during incubation at 70° for 10 minutes.
6. 200 uL of ethanol (96-100%) are added to the sample and mixed by pulse vortexing for 15 seconds. The microcentrifuge tube is centrifuged briefly to remove drops from inside the lid.
7. The mixture from step 6 (including the precipitate) is added to a QIAamp Spin Column (in a 2 mL collection tube) without wetting the rim. The cap is closed and the sample is centrifuged at 8000 rpm for 1 minute. The QIAamp Spin Column is placed in a clean 2 mL collection tube and the tube containing the filtrate is discarded.
8. The QIAamp Spin Column is opened carefully and 500 uL Buffer AW1 without wetting the rim. The cap is closed and the tube is centrifuged at 8000 rpm for 1 minute. The QIAamp Spin Column is placed in a clean 2 mL collection tube and the tube containing the filtrate is discarded.
9. The QIAamp Spin Column is opened carefully and 500 uL Buffer AW2 is added without wetting the rim. The cap is closed and the tube is centrifuged at full speed for 3 minutes.
10. The tube containing the filtrate is discarded. The QIAamp Spin Column is placed in a clean 1.5 uL microcentrifuge tube. 50 uL of EB buffer are added to the middle of the column, and left to incubate at room temperature for 15 minutes. The sample is centrifuged at 8000 rpm for 1 minute.
11. The DNA in EB buffer is stored at −20° C. indefinitely.

Alternatively, if the density of melanoma cells in a tissue sample is low (less than about 1%), additional procedures to enrich the tissue sample for melanoma cells may be performed. Additional research has shown that the sensitivity of the assay is sufficient to detect ~1% density of melanoma cells, rather then 10% as originally estimated. One such procedure is Laser Capture Microdissection (LCM). The governing principle of LCM is that tissues on a microscope slide that have been rendered reactive by treatment with laser energy can be transferred to a special coverslip. Briefly, 5-10 μm sections of tumor material are cut from paraffin blocks and mounted onto uncharged glass slides. These sections are subjected to hematoxylin and eosin staining but not coverslipped. A 5 μm section is also processed and coverslipped to facilitate analysis of the microdissection. Tissues to be microdissected are viewed through a video microscope, such as a second-generation Arcturus PixCell II microscope (Arcturus, Mt. View, Calif.). The position of the slide is adjusted so the desired cells are localized under the targeting light. Activation of the laser causes the desired cells to be transferred to the special coverslip, which is mounted on a plastic cap. Microdissection of melanoma cells is accomplished with a 30 μM spot size, amplitude of 100 mW, voltage of 305 mV, and a pulse width of 80 msec. The dissected material is reviewed for morphology, and non-specific transfers such as adjacent keratinocytes, which have not been laser activated but are carried with the melanoma cells onto the cap, are easily removed by softly tapping the cap on the "scotch tape like" Arcturus Prep Strips. The sample is placed into a tube containing 30 μl of Proteinase K digestion buffer (Arcturus) and incubated for a minimum of 16 hours at 65° C. After this incubation, Proteinase K is inactivated by heating the sample for 10 minutes at 95° C. 1 to 3 μl of this preparation is used for PCR amplifications. Using such techniques, it is possible to amplify DNA from as few as 20 cells.

DNA is also isolated from peripheral blood as follows, using the QIAamp DNA Blood Mini Kit Handbook protocol.

DNA Isolation from Blood:
1. 20 uL of Qiagen Proteinase K is pipetted into the bottom of a 1.5 mL microcentrifuge tube
2. 200 uL of sample (up to 200 uL whole blood, plasma, serum, or buffy coat) are added.
3. 200 uL of Buffer AL are added to the sample. The sample is mixed by pulse-vortexing for 15 seconds.
   *If the sample volume is larger than 200 uL, the amount of Qiagen Proteinase K and Buffer AL are increased proportionally.
4. The sample is incubated at 56° for 10 minutes.
   *DNA yield is maximal after lysis for 10 minutes. Longer incubation times have no effect on yield or quality of the purified DNA.
5. The remainder of the protocol follows Steps 6-11 of the tissue protocol described above.

PCR conditions are described below. An example is given for the mutant specific primers FR2, or R3. These primers are paired with WT Reverse (15R), or WT Forward (15F), respectively. Similar conditions are used for different primer pairs. Typically, only the primer concentrations and annealing temperatures will change.

| 20 uL PCR reaction: FR2 primer | | 20 uL PCR reaction: R3 primer | |
|---|---|---|---|
| REAGENT | uL | REAGENT | uL |
| H₂0 | 5.5 | H₂0 | 5.5 |
| 10x Buffer | 2 | 10x Buffer | 2 |
| 10 uM dNTP | 0.4 | 10 uM dNTP | 0.4 |
| BRAF 15FR2 (10 uM) | 2 | BRAF 15F (10 uM) | 2 |
| BRAF 15R (10 uM) | 2 | BRAF 15R3 (10 uM) | 2 |
| Taq | 0.1 | Taq | 0.1 |
| DNA | 8 | DNA | 8 |
| T: 62°, 50 cycles | | T: 60°, 50 cycles | |

*The above charts indicate PCR reagents for one 20 uL reaction. Reagent volumes are multiplied proportionally for each additional sample.

1. PCR reagents and DNA are placed on ice.
2. H₂0, dNTP, and primers are added to one microcentrifuge tube ("Tube A"). Buffer and Taq polymerase are added to a second tube ("Tube B").
3. Solution in tube A is added into labeled 8-per-strip (200 uL) tubes.
4. DNA is added to 8-per strips containing solution A.
5. Solution in tube B is added to each sample.
6. 8-per-strip tubes are sealed tightly and PCR reaction is carried out at the appropriate annealing temperatures.
7. Amplified DNA bands are visualized on a 2% agarose gel, or ABI 310, when fluorescently labeled primers are used.

Kits

In yet another aspect, the present invention also provides kits for diagnosing, evaluating, and/or monitoring melanoma in a mammal. An exemplary kit contains a container or a sample vial for storing a sample of a tissue or a body fluid; a composition comprising at least one BRAF mutant-specific PCR primer pair in an amount effective to permit detection of BRAF mutant nucleic acid sequence in a sample; and an instructional material which directs use of the composition for detecting the presence and/or determining the amount of a BRAF mutant nucleic acid sequence.

As used herein, an "instructional material" includes a publication, recording, diagram, or any other medium of expression that directs or dictates the use of the components of a kit for performing the function of a method of the invention described herein. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

With regard to a composition for inclusion in a kit, detection reagents such as BRAF mutant specific primers and BRAF mutant specific PCR primer pairs are as described herein in the inventive methods and compositions. The composition comprises at least one set of BRAF mutant specific PCR primer pairs in an amount effective to permit detection of BRAF mutant nucleic acid sequence in the sample. Detection of BRAF mutant nucleic acid sequence is accomplished using any of the methods described herein or known to a skilled artisan for detecting a specific nucleic acid molecule in a biological sample or isolated from a biological sample.

In addition to BRAF mutant specific primer pairs as described above, a kit may also comprise buffers, nucleotide bases, and other compositions to be used in hybridization and/or amplification reactions. Each solution or composition may be contained in a vial or bottle and all vials held in close confinement in a box for commercial sale.

Positive and negative control nucleic acid sequences (e.g., oligonucleotides) of the BRAF exon 15 sequence are also included in the above kits. The positive control comprises the T to A "hotspot" mutation at the appropriate position in the oligonucleotide sequence to correspond to the T1799A mutation described in human melanomas. The negative control oligonucleotide comprises a "T" at that amino acid coordinate, corresponding to the normal or wild-type sequence. An oligonucleotide is of sufficient length to allow hybridization of all the primers described in the accompanying Figures and Tables. When the assay is performed properly, an amplification product is generated in reactions containing the positive control oligonucleotide, but not in reactions which contain the negative control oligonucleotide.

Unless otherwise indicated, the present invention utilizes standard techniques well known to practitioners of molecular biology and described in several laboratory protocol handbooks, including: *Molecular Cloning: A Laboratory Manual*, Sambrook et al. eds., Cold Spring Harbor Laboratory Press (1989); Ausubel et al. eds., *Current Protocols in Molecular Biology*, John Wiley & Sons, NY, N.Y. (1995).

EXAMPLE I

PCR-Based Assay for Detecting BRAF Mutant Nucleic Acid Sequences

Although anatomic imaging studies, such as chest X-ray, magnetic resonance imaging (MRI), CT, and positron emission transmission (PET) lack the resolution to detect the onset of metastatic processes, these approaches are used routinely to monitor patients for disease recurrence and to select patients at high risk for the development of metastases. The inadequacy of these imaging methods is underscored by the fact that tumor cell deposits at distant sites can take months to grow into metastasized disease detectable by these means. Elevation of serum LDH, an indirect marker of tumor burden, has been associated with progressive disease in several studies, but it has not been adopted at all melanoma centers as a useful monitoring test (reviewed in Hwu et al. 2003, supra). The TA-90 blood test has also shown promise, but multi-institutional validation studies have not yet been performed (reviewed in Hwu et al. 2003, supra).

Many investigators have attempted to develop a circulating tumor cell assay for melanoma. First described in 1991, the most commonly used assay is based on the detection of mRNA for tyrosinase in the peripheral blood using RT-PCR (Smith et al. Lancet 1991; 338:1227-9). Tyrosinase is a central enzyme in the melanin biosynthetic pathway. As such, it is expressed in melanocytes, which are not known to circulate, so its detection in the peripheral blood is abnormal. Results among melanoma patients, however, have varied widely (0% to 100% sensitivity), even among stage IV patients in whom the chances of detecting melanoma cells in the circulation are greatly enhanced (reviewed in Ghossein et al. Recent Results Cancer Res 2001; 158:63-77; Tsao et al. Arch Dermatol 2001; 137:325-30). Further disappointment was evident in a multi-institutional collaborative study where 4/9 (44%) laboratories had unacceptable sensitivity or specificity for samples derived from normal volunteers, wherein the samples had been spiked in vitro with different numbers of cultured melanoma cells (Keilholz et al. Eur J Cancer 1998; 34:750-3). Variability in results was most likely due to differences in sample preparation, RNA extraction, or cDNA synthesis, as all laboratories were able to assay correctly the cDNA standards distributed.

In addition to variability resulting from differences in technical expertise, RNA-based assays for detecting circulating tumor cells are associated with other problems. False positives can be due to the general process of "illegitimate transcription" (i.e., expression of tissue specific genes in non-specific cells), or the presence of pseudogenes (Kaplan et al. Hum Mutat 1992; 1:357-60). Finally, RNA-based assays inherently rely on circulating melanoma cells to express the genes of interest (e.g., tyrosinase). Interactions between tumor cells and their microenvironment can influence gene expression (Hendrix et al. Oncogene 2003; 22:3070-5), so it is possible that some melanoma cells may not express tyrosinase once they enter the peripheral circulation.

Many of the problems correlated with RNA-based assays for detecting circulating tumor cells can be avoided using DNA-based techniques, which eliminate issues relating to transcription of mRNA and the steps of cDNA synthesis. Also, DNA is inherently more stable than RNA, so variations in sample preparation protocols are not as critical as in RNA-based analyses. Indeed, peripheral blood DNA-based assays are routinely used to monitor patients with HIV and Hepatitis B for response to treatment, and are beginning to be used under certain circumstances in oncology.

DNA-based techniques for detecting tumor cells in clinical specimens have been applied in bladder, pancreatic, lung and colon cancers (reviewed in Sidransky. Science 1997; 278: 1054-9). These techniques take advantage of two features of these cancers: 1) mutation in the K-RAS or TP53 genes is common; and 2) hotspot mutations exist, simplifying the detection strategy. This strategy has also been employed to detect tumor cells in the blood of patients with colorectal cancer (Iinuma et al. Int J Cancer 2000; 89:337-44). The assay detected 10 cells in $10^7$ normal peripheral blood mononuclear cells. Among patients in whom mutant K-RAS or TP53 could be demonstrated in the tumor specimens, 45% had detectable cells in their blood. Although the cohort was small (only 20 patients), a significantly shorter survival was demonstrated for patients with circulating tumor cells (p=0.03).

Currently, the greatest uncertainty in melanoma management is in the prognosis of patients with tumors of intermediate thickness (1.0-4.0 mm). Patients with tumors less than 1.0 mm in thickness have an excellent prognosis, while those with tumors greater than 4.0 mm thick have a poor prognosis. For the intermediate group, the lack of tools with which to accurately predict metastatic potential is particularly profound. The efforts of a clinician monitoring a melanoma patient rendered disease-free by surgical or medical treatment are equally limited. As indicated herein above, imaging tests utilized for monitoring patients to detect early development of metastatic spread require significant cellular proliferation to facilitate visualization.

As indicated herein above, mutations in the BRAF oncogene have been discovered in up to 80% of melanoma tissues, frequencies strikingly higher than any other molecular alteration in this disease. Such mutations are frequently accompanied by increases in gene-copy number (Bastian. 2003, supra). BRAF mutations have also been detected in tumor tissues from other types of cancer. Experimental studies have demonstrated that several BRAF mutations, especially the T1799A hotspot mutation, which accounts for 90% of BRAF mutations in melanoma, can transform fibroblasts in culture. Most recently, experiments blocking the expression of mutant BRAF in melanoma cell culture were shown to inhibit cell growth and promote cell death, suggesting that BRAF inhibitors could bolster melanoma treatment significantly. To date, there are no published studies detecting mutant BRAF in the peripheral blood of melanoma or any other cancer patients.

The methods and materials used by the present inventors are described herein above.

Results

The present inventors have analyzed BRAF and N-RAS mutations in 77 metastatic melanoma tumor specimens and 11 melanoma cell lines (Gorden et al. 2003, supra). To this end, BRAF exons 11 and 15, and N-RAS exons 2 and 3 were amplified and sequenced. Mutations in 36 of 77 (47%) tissue specimens and 8 of 11 (73%) cell lines were detected. Ninety-two percent of mutations in tissues occurred in BRAF exon 15, and 31 of 33 (94%) exon 15 mutations consisted of the previously identified T1799A (formerly numbered as T1796A) nucleotide substitution.

As described herein, the present inventors have developed a novel method involving a PCR amplification strategy that specifically amplifies the T1799A mutant. The present method is useful for detecting circulating melanoma cells and, thus, may be used advantageously to diagnose melanoma in a subject, detect metastasis of a primary melanoma in a subject, and/or assess the therapeutic efficacy of a drug or compound administered to treat a subject with melanoma. To this end, novel oligonucleotide primers that specifically amplify alleles comprising the T1799A hotspot mutation of BRAF have been designed and tested using the polymerase chain reaction (PCR). A diagram of this amplification strategy is shown in FIG. 1B, which depicts BRAF exon 15 flanked by intronic sequences (thin lines). The intronic primers (wtFwd and wtRev) have been previously described by Davies et al. (2002, supra) and Gorden et al. (2003, supra). Mutant primers (mRev1, SEQ ID NO: 1; mRev2, SEQ ID NO: 2; mFwd1, SEQ ID NO: 3; mFR-2, SEQ ID NO: 6; and mR3, SEQ ID NO: 7) are novel primer sequences.

A primer such as the wtFwd primer (SEQ ID NO: 4) may be combined with either mRev1, mRev2, or mR3 to form a BRAF mutant specific PCR primer pair. In that mRev1, mRev2, and mR3 are designed to hybridize or anneal specifically to a BRAF mutant allele, amplification products generated by PCR amplifications using these primers are specifically generated from BRAF mutant templates. Alternatively, mFwd1, which binds to the non-coding strand of the BRAF mutant, may be combined with wtRev to form a BRAF mutant specific PCR primer pair, which is capable of amplifying the mutant allele.

marker D9S2136 were analyzed using a 1.5% agarose gel (top panel) and ABI 310 Genetic Analyzer (bottom panel). Reliable detection in agarose is limited to amounts of 20 ng or greater, whereas the sample shows peaks at 3 times baseline at 0.1 ng. Use of fluorescently tagged PCR products and appropriate means for visualizing these products, therefore, results in a 200-fold improvement in detection.

Accordingly, in embodiments wherein PCR products are fluorescently labeled, one or both primers of PCR primer pair used to amplify a BRAF mutant nucleic acid sequence are fluorescently tagged with, for example, 6'-FAM to allow detection of PCR products using the ABI 310 Genetic Analyzer and Genescan 3.1.2 software (Applied Biosystems). In one embodiment the wtFwd or wtRev primers are fluorescently tagged with, for example, 6'-FAM. Alternatively, any one of the BRAF mutant specific primers (SEQ ID NO: 1-3, 6, or 7) can be fluorescently labeled. Apart from 6-FAM, other fluorescent labels including but not limited to 5-FAM, TET, HEX, TAMRA, ROX, JOE, and NED may be used.

TABLE 1 is a list of BRAF PCR primers and predicted PCR product sizes.

| Forward Primer | Reverse Primer | Product length (bp) |
|---|---|---|
| wtFwd<br>TCATAATGCTTGCTCTGATAGGA<br>(SEQ ID NO: 4) | mRev1<br>AGATTTCTCTGTAGCTAGACCAAAA<br>(SEQ ID NO: 1) | 128 |
| wtFwd<br>TCATAATGCTTGCTCTGATAGGA<br>(SEQ ID NO: 4) | mRev2<br>ATCGAGATTTCTCTGTAGCT<br>(SEQ ID NO: 2) | 132 |
| mFwd1<br>AGCTACAGAGAAATCTCGATGGAG<br>(SEQ ID NO: 3) | wtRev<br>GGCCAAAAATTTAATCAGTGGA<br>(SEQ ID NO: 5) | 112 |
| mFR-2<br>GGTGATTTTGGTCTAGCTACATA<br>(SEQ ID NO: 6) | wtRev<br>GGCCAAAAATTTAATCAGTGGA<br>(SEQ ID NO: 5) | 125 |
| wtFwd<br>TCATAATGCTTGCTCTGATAGGA<br>(SEQ ID NO: 4) | mR3<br>ACCCACTCCATCGAGATTTAT<br>(SEQ ID NO: 7) | 140 |

The specificity of the mutant-specific primers is established by testing them on melanoma cell lines SK-MEL 85 (wild-type for exon 15, mutant for exon 11), and SK-MEL 29 (mutant for exon 15). PCR reactions using each primer set were performed at annealing temperatures of ranging from 53° C. to 68° C. Each primer showed specificity for the mutant product, as evidenced by disappearance of the wild-type band as the temperature increased. The product lengths indicated are approximate in nature, and may vary slightly.

Figure 2:
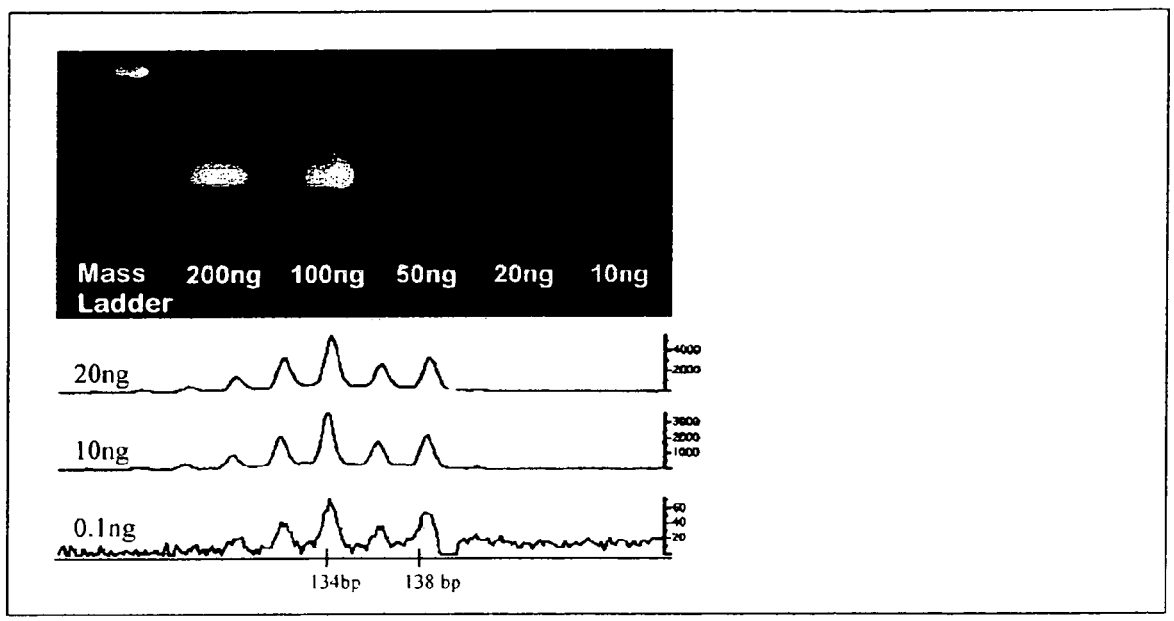
FIG. 2 shows a photograph of PCR products separated on an ethidium bromide stained agarose gel (top panel) and electropherograms of fluorescently labeled PCR products analyzed using an ABI 310 Genetic Analyzer.

To further enhance sensitivity and specificity, fluorescently labeled intronic primers (denoted WT Fwd or WT Rev), for example, may be used. Fluorescent detection of PCR products is approximately 200-fold more sensitive than detection using ethidium bromide-stained agarose gels. As shown in FIG. 2, serial dilutions of a fluorescently labeled PCR product are analyzed in parallel on an ethidium bromide-stained agarose gel and using an ABI 310 Genetic analyzer. Quantitation of the PCR products in the agarose gel using a molecular mass ladder revealed that reliable detection of the PCR products was far superior using the ABI 310 analyzer as compared to that obtainable on an ethidium bromide-stained gel.

Specifically, dilutions of fluorescently tagged PCR products from a tumor sample heterozygous for the microsatellite

EXAMPLE II

Figure 3:
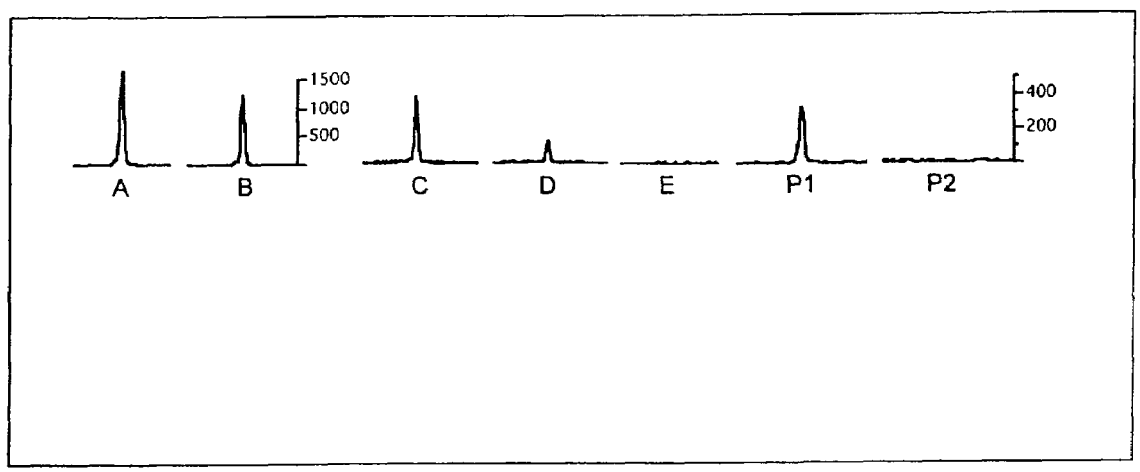
FIG. 3 shows relevant portions of electropherograms depicting the amplification product of a mutant specific PCR reaction.

Analysis of Peripheral Blood Specimens. As demonstrated herein, the method of the present invention has been used successfully to detect the hotspot BRAF T1799A substitution in a peripheral blood sample of a melanoma patient. As shown in FIG. 3, an aspect of the present method directed to utilization of fluorescent, mutant-specific primers and PCR-mediated amplification of the BRAF mutant template to produce fluorescently labeled PCR products (BRAF mutant specific amplification products) is used for this analysis.

Peripheral Blood Specimens. In general, 8 to 12 ml of blood is collected in EDTA-containing (purple-top) tubes and placed immediately on ice. The blood is subjected to erythrocyte lysis using a hypotonic buffer (e.g., 10 mM $KHCO_3$, 155 mM $NH_4Cl$, 0.1 mM EDTA, pH=7.4). The leukocytes are recovered using centrifugation and washed with 1× phosphate-buffered saline. DNA may be extracted from collected cells using, for example, the QIAmp DNA system (QIAgen, Valencia, Calif.) following protocols based on those previously described for extracting DNA from tumor cell lines (Gorden et al. 2003, supra).

PCR conditions: For this experiment, 100 ng of template DNA from the patient sample is used. The primers used are WT Fwd labeled with 6-FAM, and mR2. 45 cycles are used, the annealing temperature was 64.6° C. The reaction mixture is as described in the methods presented herein above. Such conditions are optimized to achieve detection of approximately one mutant cell in 1 ml of blood $10^7$ normal cells. Optimization of PCR conditions is well within the capabilities of a skilled practitioner.

Results

To determine the sensitivity of the assay, 25 mls of blood was drawn from a volunteer and separated into 5 ml aliquots denoted A-E, which were spiked with decreasing numbers of the BRAF mutant SK-MEL 29 cell line. See Table 2. DNA was extracted from the specimens and the concentrations were standardized. DNA from samples A-E is subjected to mutant-specific PCR using fluorescently tagged primers. In addition, DNA from the peripheral blood of eight melanoma patients enrolled in the NYU-Interdisciplinary Melanoma Cooperative Group (NYU-IMCG) is tested in parallel.

Table 2 shows the composition of samples A-E spiked with the indicated numbers of BRAF mutant cells.

| Sample | SKMel#29 cells added |
|---|---|
| A | 3,000 |
| B | 500 |
| C | 50 |
| D | 5 |
| E | 0 |

As shown in FIG. 3, the present method enables fluorescent detection of the BRAF exon 15 T1799A mutation in peripheral blood samples. Relevant portions of electropherograms depicting the product of the mutant specific PCR reaction are shown. The x-axis represents fragment size; the y-axis is relative fluorescent units (RFU) corresponding to PCR product quantity. Note that RFU scales are different for panels A and B, as opposed to panels C-E, P1, and P2. The difference in scale was necessitated to accommodate the increased fluorescent signal associated with the increased number of mutant cells added to spiked samples A and B. Panels A-E correspond to the spiked samples A-E described above; panels P1 and P2 are patient samples. For reference, sample D contains the fewest mutant cells, with 5 cells added to 5 ml of blood, yet a peak is still clearly visible above baseline.

As indicated above, panels P1 and P2 pertain to DNA extracted from peripheral blood samples of two Stage IV melanoma patients. Patient 1 (P1) is clearly positive for a BRAF mutant allele as detected by the present method. All six patients with localized disease (Stage I/II) were negative.

The results determined for the spiked samples (A-E) demonstrate that the sensitivity of the assay enables the ready detection of 1 BRAF mutant melanoma cell in 1 ml of human blood. Most importantly, the analyses performed on samples isolated from melanoma patients clearly demonstrate that the present method can detect mutant BRAF in the peripheral blood of a patient with Stage IV melanoma.

Under circumstances wherein improved sensitivity is desired, an immunomagnetic-based negative selection strategy may be used to reduce the number of leukocytes in the sample prior to DNA extraction. A similar strategy using anti-CD45 antibodies showed a nearly 10-fold increase in sensitivity for circulating colon cancer cells (Iinuma et al. 2000, supra).

EXAMPLE III

The present inventors have also designed additional primers that have been further optimized to be of utility in the methods of the present invention that are directed to detecting BRAF mutations in circulating melanoma cells. These primers are designated mFR-2 and mR3, which are described herein in Table 1 and FIGS. 1A, 1B, and 4. The initial design of the mFR-2 and mR3 primers was based on primers described in Xu et al. and used in their analysis of BRAF mutations in papillary thyroid carcinoma (Xu et al. Cancer Res, 63: 4561-4567, 2003). The sequences of the mFR-2 and mR3 primers have, however, been altered to improve the specificity with which these primer sequences bind to mutant as opposed to wildtype BRAF sequences. Briefly, the primers comprise alterations in the 3' end that prevent binding to the wild-type sequence, but allow binding to the mutant sequence.

Methods and Materials

Patients: The NYU-IMCG is actively accruing patients with Stage I-IV melanoma who are under the care of NYU Surgical Oncologists, Medical Oncologists, and Dermatologists. Patient information is prospectively entered into a computerized database that includes links to all tissue specimen numbers. In addition, peripheral blood specimens are collected and stored at the time of entry into the study. To date, the IMCG has enrolled over 310 patients during the course of 26 months. Additional patients are accrued at a rate of 16-20 patients per month. As controls, blood samples from normal volunteers are also tested.

Specimen Collection: Blood is drawn into two EDTA-containing (purple-top) tubes and put immediately onto ice. Specimens are transported to the laboratory where they are processed for DNA extraction.

DNA isolation from blood samples: Cells and plasma are separated using standard centrifugation. The plasma supernatant is transferred to a clean tube, and 1 ml aliquots are placed into 1.5 ml microcentrifuge tubes. Pelleted cells are separately transferred to 1.5 ml microcentrifuge tubes. All samples are stored at −80° C. For isolation of DNA from plasma, 1 ml of plasma is thawed at room temperature and centrifuged at 16,000 rpm in an Eppendorf Model 5415R microcentrifuge. The supernatant is discarded and the pellet is resuspended in 200 µl TE buffer. This material is used to isolate DNA using the QIAmp DNA Blood Mini Kit (QIAgen, Valencia, Calif.). For isolation of DNA from cells, 200 µl of pelleted cells are used as the starting material for the QIAmp DNA Blood Mini Kit.

PCR amplification and detection of mutant BRAF alleles: The following protocol was developed for the mutant specific primers FR2 or R3. These primers are paired with WT Reverse (15R), or WT Forward (15F), respectively.

| 20 uL PCR reaction: FR2 primer | | 20 uL PCR reaction: R3 primer | |
|---|---|---|---|
| REAGENT | uL | REAGENT | uL |
| H₂0 | 5.5 | H₂0 | 5.5 |
| 10x Buffer | 2 | 10x Buffer | 2 |
| 10 uM dNTP | 0.4 | 10 uM dNTP | 0.4 |
| BRAF 15FR2 (10 uM) | 2 | BRAF 15F (10 uM) | 2 |
| BRAF 15R (10 uM) | 2 | BRAF 15R3 (10 uM) | 2 |
| Taq | 0.1 | Taq | 0.1 |
| DNA | 8 | DNA | 8 |
| T: 62°, 50 cycles | | T: 60°, 50 cycles | |

*The above charts indicate PCR reagents for one 20 uL reaction. Reagent volumes are multiplied proportionally for each additional sample.

Generally, PCR reagents and DNA are placed on ice. H₂0, DNTP, and primers are added to one microcentrifuge tube ("Tube A"). Buffer and Taq polymerase are added to a second tube ("Tube B"). The solution in tube A is added into labeled 8-per-strip (200 uL) tubes and DNA is added to 8-per strips containing solution A. The solution in tube B is the added to each sample. The 8-per-strip tubes are sealed tightly and the PCR amplification is carried out at the appropriate annealing temperatures. Amplified DNA bands are visualized on a 2% agarose gel or with an ABI 310 Genetic Analyzer when fluorescently labeled primers are used.

With respect to results presented in Example m, the wtRev primer is fluorescently tagged with 6'-FAM to allow detection of PCR products using the ABI 310 Genetic Analyzer and Genescan 3.1.2 software (Applied Biosystems). Qiagen HotStar Taq is used for all amplifications following the manufacturer's instructions. In addition, each 20 µl reaction contains 100 ng to 300 ng of genomic DNA, 0.1 µM of each primer and 2 µM dNTP mix. The annealing temperature is 62° C.; 50 cycles are performed.

Each sample may be assayed twice to confirm a result, either positive for a mutation, or negative for wild-type. In the event of discordant results, an assay is repeated for a third time. The final determination is based on the result of the third assay. In all experiments, DNA from the BRAF mutant cell line SK-MEL 29 is used as a positive control; placental DNA is used as a negative control for the mutant-specific PCR, and as a positive control for amplification with the intronic (wild-type) primers. Samples with no DNA are also included as negative controls in all experiments. As an internal control, the intronic primers wtFwd and wtRev are used to amplify the entire BRAF exon 15 to confirm that usable DNA is present in each sample. Lack of mutant BRAF amplification in a sample with positive amplification of the entire BRAF exon 15 (internal control) is interpreted as a mutation-negative case.

Results

Figure 4:
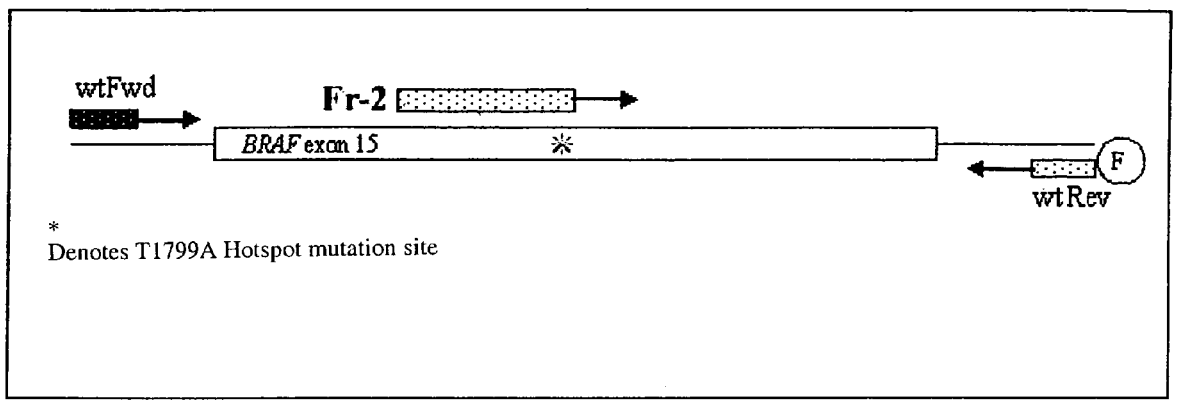
FIG. 4 shows a diagram depicting BRAF exon 15 flanked by intronic sequences (thin lines) and an alignment of the BRAF specific PCR primer Fr-2.

As indicated herein above, the present inventors have designed and tested a set of primers that amplify mutant BRAF alleles without amplifying the normal allele. A diagram of this amplification strategy is shown in FIG. 4, which depicts BRAF exon 15 flanked by intronic sequences (thin lines). The asterisk denotes the site of the BRAF hotspot mutation, T1799A. Intronic primers (wtFwd and wtRev) are those described previously Gorden et al. (2003, supra) and first described by Davies et al. (2002, supra). For the mutant specific PCR, the wtRev primer is combined with FR-2, which selectively amplifies mutant alleles, but is unable to amplify the wild-type allele due to lack of hybridization at the 3' end. FR-2 is based on primers described by Xu et al. in their study of BRAF mutation in papillary thyroid carcinomas (Xu et al. 2003, supra). The present inventors have rendered a change to a nucleotide at the 3' end of the primer to decrease the likelihood that the primer will bind non-specifically to the wild-type sequence. Of note, the primer does still recognize the less common BRAF tandem mutations encoding V600K and V600E (Gorden et al. 2003, supra; Kumar et al. 2003, supra; Pollock et al. 2003, supra).

Figure 5:
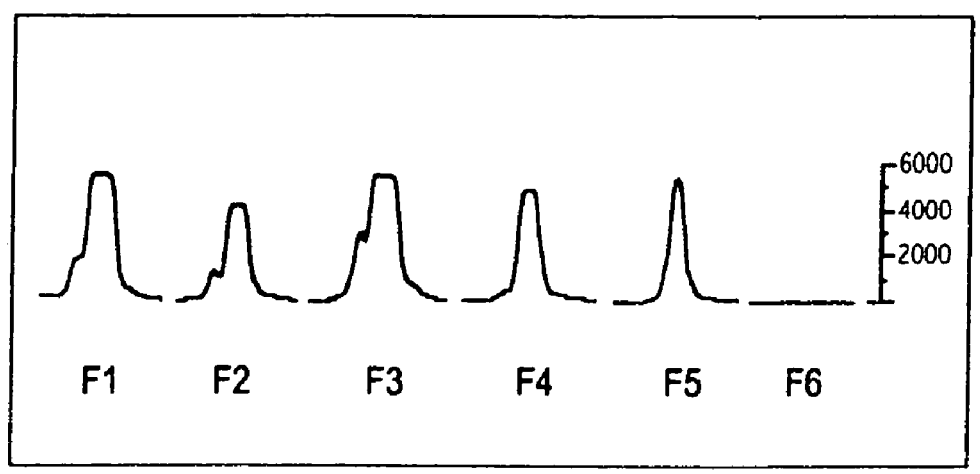
FIG. 5 is a plot showing detected levels of fluorescent intensity correlated with PCR product generated.

To determine if the mFR-2 and mR3 primers are useful tools for detecting mutant BRAF alleles in peripheral blood, a titration experiment was performed. Twenty-five milliliters of blood was drawn from a normal volunteer and separated into 5 ml aliquots denoted F1-F6, which were spiked with decreasing numbers of the BRAF mutant SK-MEL 29 cell line (Table 3). DNA was extracted from the specimens and the concentrations were standardized. In FIG. 5, DNA from these samples was subjected to the mutant-specific PCR using fluorescently tagged primers. The results presented in Example III were generated using the mFR-2 primer.

Table 3 shows the composition of samples F1-F6 spiked with the indicated numbers of BRAF mutant cells.

| Sample | SKMEL29 Cells Added |
| --- | --- |
| F1 | 100,000 |
| F2 | 5,000 |
| F3 | 500 |
| F4 | 50 |
| F5 | 5 |
| F6 | 0 |

As shown in the FIG. 5, peaks running at 121 bp (corresponding to the size of mutant BRAF PCR product) are readily apparent in samples in which mutant cells were added (F1-F5). No peak is detected in the sample comprising only normal blood cells, but no tumor cells (F6). Likewise, the primers fail to amplify a product when normal, placental DNA is used as the template. While the peak heights did not decrease with decreasing amounts of mutant cells in this experiment, the peak areas decrease, as evidenced by the narrowing of the peak widths (compare F1 and F5).

The present inventors have also tested this assay on DNA extracted from peripheral blood cells from nine patients enrolled in the NYU-IMCG. The clinical details pertaining these patients are listed in Table 4.

TABLE 4

| Patient # | Gender | Age | Stage at time of primary diagnosis | Disease-Free Survival* | Site of recurrence/met | BRAF status |
| --- | --- | --- | --- | --- | --- | --- |
| 04-75 | Female | 70 | IA | 39 months | In transit/sat | Mutant |
| 04-47 | Male | 72 | IIIB | 1 month | In transit/sat | Wild-type |
| 04-71 | Male | 68 | NA** | 3 months | In transit | Wild-type |
| 04-66 | Male | 54 | IIIC | At presentation | LN | Wild-type |
| 04-49 | Female | 54 | IA | 10 years | Lung | Wild-type |
| 04-01 | Female | 53 | IIIA | 26 months | Extra-regional cutaneous | Wild-type |
| 04-86 | Female | 82 | IIIB | At presentation | In transit/sat | Mutant |
| 04-51 | Male | 26 | IB | 22 months | Local recurrence | Mutant |
| 04-63 | Female | 50 | IIA | 7 years | Extra regional cutaneous | Mutant |

Figure 6:
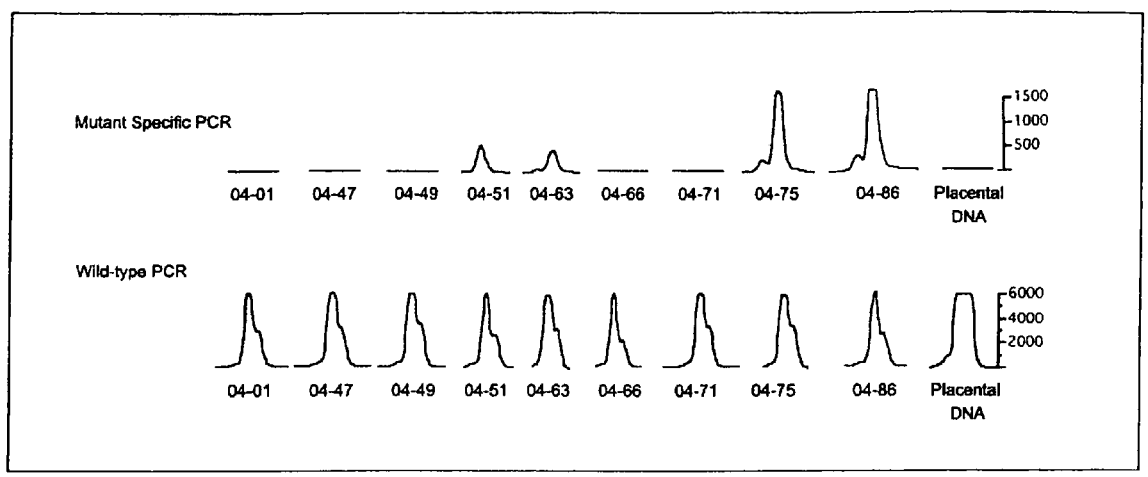
FIG. 6 is a plot showing detected levels of fluorescent intensity correlated with PCR product generated.

*Time between diagnosis of the primary and diagnosis of the first recurrence/metastasis
**Unavailable information; stage at diagnosis could not be verified As shown in FIG. 6, 4/9 (44%) of these patients had detectable mutant BRAF alleles in their peripheral blood (upper panel). All patients had detectable wild-type BRAF as expected (lower panel). The control, placental DNA sample failed to amplify mutant BRAF, but did amplify the wild-type BRAF.

Figure 7:
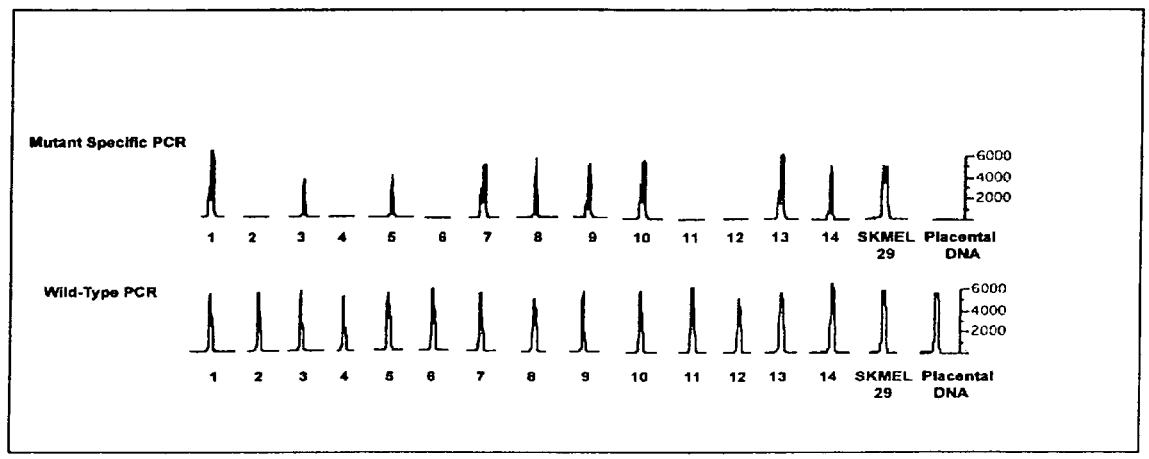
FIG. 7 is a plot showing detected levels of fluorescent intensity correlated with PCR product generated.

The inventors have further extended their results to examine the robustness of the present method for testing plasma samples from 14 patients with metastatic melanoma. Overall, 8/14 (57%) patients had detectable mutant BRAF alleles in their plasma. This included 6/10 (60%) patients who died of their disease (FIG. 7).

The data presented herein demonstrate that the method of the present invention is a viable assay for detecting circulating melanoma cells using a PCR based approach. The present inventors anticipate that these results will be further corroborated when this approach is applied to larger patient cohorts.

Figure 8:
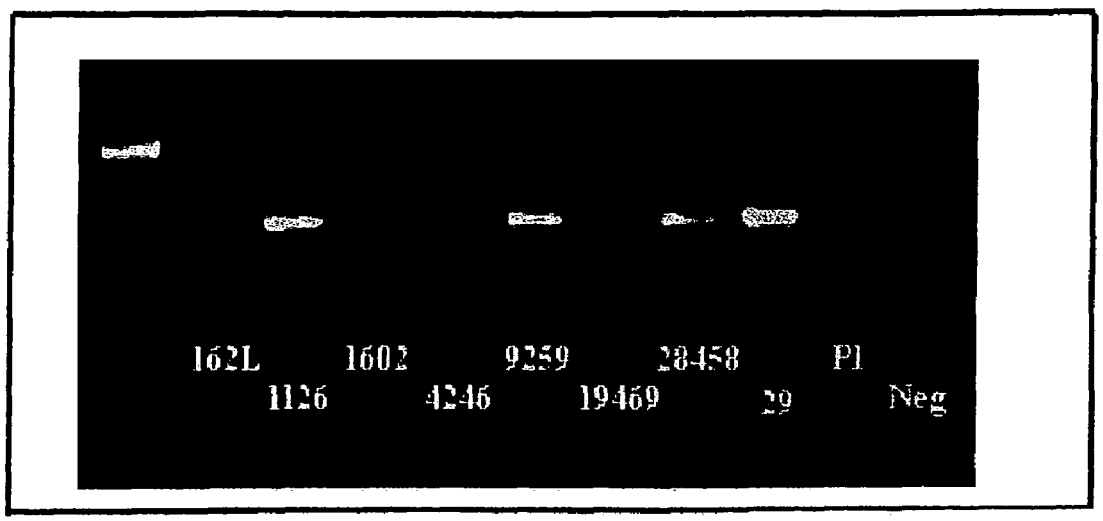
FIG. 8 shows a photograph of PCR products separated on an ethidium bromide stained agarose gel.

The present inventors have also analyzed BRAF mutations in primary melanomas. To date, DNA has been extracted from thirty formalin-fixed, paraffin embedded primary melanomas and mutant-specific PCR has been performed on these samples. The range of tumor thickness was 0.5 mm to 11.6 mm, with a median tumor thickness of 4.0 mm. An example of this analysis is shown in FIG. 8. For this analysis, a single 5 µm section was used as the source of DNA from each of 7 patients. Patient sample numbers are listed below the lanes. #29 is the positive control SK-MEL 29 cell line. PI is an abbreviation for placental DNA (negative control), as it lacks the mutant BRAF; Neg is an abbreviation for the no DNA, negative control. At the far left are molecular weight markers. As shown in FIG. 8, 3/7 (43%) patient samples show a positive result.

To date, a BRAF mutation has been detected in 17/30 (57%) cases examined. Thus, the primers and methods of the present invention may be used to advantage to determine BRAF mutation status in both solid tumor samples as well as in fluid samples such as blood and plasma. The applicability of the present method to the analysis of primary melanomas is particularly critical with respect to patients wherein metastasis is evident because it is usually much easier to isolate a sample from a primary melanoma than from metastatic tissue, which tends to be distributed to more internal locales. An accurate diagnosis of BRAF mutation status can thus be achieved using the methods and primers described herein to evaluate fluid (e.g., blood, plasma, or lymph) or solid (e.g., primary melanoma) samples isolated from a patient. The ability to determine rapidly and definitively the BRAF status of a melanoma cell isolated from a patient accelerates the speed with which a practitioner can prescribe appropriate medications for such a patient. If, for example, the results demonstrated that a sample isolated from a patient comprised mutated BRAF sequences, that patient would be a suitable candidate for treatment with one of the available BRAF inhibitors.

EXAMPLE IV

The method of the present invention was also evaluated using quantitative PCR. An ABI 7900HT Fast Real-Time PCR System (Applied Biosystems, Inc.) was used to demonstrate that mutant specific-PCR (MS-PCR) reaction is well suited for quantitative PCR detection. Accordingly, the present inventors used the primers SEQ ID NO: 5 and SEQ ID NO: 6 (mFR-2 and wtRev) to amplify the mutant BRAF allele from a series of dilutions of SKMEL 29 cell line DNA (mutant for BRAF). For each dilution, exon 1 of the HRAS gene was also amplified and will be used as an internal control for patient samples, using previously published primers (Bastian et al. Cancer Res 2000: 60:1968-73). According to published reports, mutations, deletions or increased copy numbers of HRAS in melanoma are extremely rare (Bastian et al. 2000. supra), and BLAST search of these primers show that they are not expected to amplify any pseudogenes. Quantitative detection was done using the SYBR Green detection format. The dissociation curve in FIG. 9A demonstrates the specificity of both BRAF and HRAS primers. The small peak noted in the HRAS curve likely arises late in amplification (after detection of the threshold cycle number). In FIG. 9B, linear regression of the median Ct values ($N \leq 3$) versus log DNA input demonstrate the large dynamic range and accuracy of the real-time quantitative PCR method, with $R^2$ values of 0.9825 (BRAF) and 0.9995 (HRAS). Linear regression of dilutional experiments reveals that the cycle threshold is proportional to the log DNA template concentration. Error bars represent standard deviation from triplicate wells. These data demonstrate that the relative abundance of mutant BRAF alleles from samples with as little as 0.1 ng of DNA can be measured.

EXAMPLE V

TaqMan PCR technology may also be used to achieve quantitative PCR. In this approach, a specific oligonucleotide probe is designed to bind to the PCR product generated by a PCR reaction. The PCR reaction uses the previously described primers FR2 and wtRev (SEQ ID NOs: 6 and 5, respectively). The probe is labeled at the 5'end with a fluorescent reporter dye, and at the 3' end with a quencher dye. As PCR amplification proceeds, the probe binds the PCR product. The bound probe is digested by the 5' nuclease of the AmpliTaq Gold polymerase, resulting in the separation of the quencher dye from the reporter dye. Cleavage of the probe results in an increase in fluorescence emitted from the reporter dye, which is monitored in the reaction tube. This increase in fluorescence is related to the amount of mutant BRAF DNA in the sample, and only occurs in the presence of the target sequence, making the technique highly specific for the mutant BRAF PCR product.

PCR Amplification and Detection: Two different Braf Exon 15 probes were designed BRAF 1 Probe 1 (CAA ACT GAT GGG ACC CAC TC; SEQ ID NO: 9) and BRAF 2 Probe 2 (ACC ATC CAC AAA ATG GAT CC; SEQ ID NO: 10), to which a 5'FAM fluorescent covalently linked reporter dye and a 3' non-fluorescent quencher are attached. TaqMan Universal PCR Master Mix (Applied Biosystems, Foster City, Calif.) kit may be used following the recommended protocol of a final concentration of 1× in a final volume of 10 µl. Final forward (FR2) and reverse (R) primer concentration of 500 nM and TaqMan probe (BRAF 1, BRAF 2) concentrations of 250 nM may be used as optimal conditions for the assay. A titration of mutant cell line SKMEL 29 DNA ranging from 50 ng, 25 ng, 12.5 ng, 6 ng, 3 ng and 0 ng may be used as the template. All conditions are done in triplicate to ensure reproducibility of the results. PCR products may be amplified using an initial of 95° C., for 10 minutes for AmpliTaq Gold Activation, followed by 40 cycle parameters of 95° C., for 15 seconds to denature and 60° C. to anneal/extend.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for diagnosing metastatic melanoma in a subject, said method comprising:
   (a) isolating a blood sample from said subject, wherein the blood sample comprises DNA sequences;
   (b) performing an amplification reaction of said DNA sequences of said blood sample, wherein said amplification reaction comprises a first primer capable of annealing specifically to a BRAF mutant sequence at a first position in a BRAF DNA sequence wherein said first primer is SEQ ID NO: 6 and a second primer capable of annealing specifically at a second position in a BRAF DNA sequence, wherein said first and second primers anneal to different strands of double stranded BRAF DNA sequence, wherein the amplification reaction is capable of producing a BRAF mutant specific amplification product when the DNA sequences of the sample comprise a BRAF DNA sequence comprising a mutant sequence at said first position of said BRAF DNA sequence; and
   (c) visualizing amplification products produced by said amplification reaction, wherein detection of a BRAF mutant specific amplification product is a positive indicator of metastatic melanoma in said subject.

2. The method of claim 1, wherein the blood sample is peripheral blood.

3. The method of claim 2, further comprising removing erythrocytes from said peripheral blood prior to step (b) to produce a population of erythrocyte-depleted peripheral blood cells.

4. The method of claim 1, further comprising isolating DNA sequences from said blood sample.

5. The method of claim 1, wherein said BRAF mutant sequence at a first position in a BRAF nucleic acid sequence comprises a T1799A mutation in BRAF exon 15.

6. The method of claim 1, wherein said second primer capable of annealing specifically at a second position in a BRAF nucleic acid sequence is SEQ ID NO: 4 or SEQ ID NO: 5.

7. The method of claim 1, wherein said method further comprises a preliminary amplification reaction of said DNA sequences of said sample performed prior to the amplification reaction of step (b), and wherein said preliminary amplification reaction comprises first and second primers capable of annealing specifically to a BRAF DNA sequence, wherein said first and second primers anneal to different strands of double stranded BRAF DNA sequence; and said preliminary amplification reaction produces a BRAF amplification product capable of amplification using said first and second primers of step (b).

8. The method of claim 1, wherein at least one of said first or second primers is fluorescently labeled and amplification products produced by said amplification reaction are fluorescently labeled.

9. A method for detecting metastatic melanoma in a subject, said method comprising:
   (a) isolating a blood sample from said subject, wherein the blood sample comprises DNA sequences;
   (b) performing an amplification reaction of said DNA sequences of said sample, wherein said amplification reaction comprises a first primer capable of annealing specifically to a BRAF mutant sequence at a first position in a BRAF DNA sequence, wherein said first primer is SEQ ID NO: 6 and a second primer capable of annealing specifically at a second position in a BRAF DNA sequence, wherein said first and second primers anneal to different strands of double stranded BRAF DNA sequence, wherein the amplification reaction is capable of producing a BRAF mutant specific amplification product when the DNA sequences of the sample comprise a BRAF DNA sequence comprising a mutant sequence at said first position of said BRAF DNA sequence; and
   (c) visualizing amplification products produced by said amplification reaction, wherein detection of a BRAF mutant specific amplification product is a positive indicator of metastatic melanoma in said subject.

10. The method of claim 9, wherein the blood sample is peripheral blood.

11. The method of claim 9, further comprising removing erythrocytes from said peripheral blood prior to step (b) to produce a population of erythrocyte-depleted peripheral blood cells.

12. The method of claim 9, further comprising isolating DNA sequences from said blood sample.

13. The method of claim 9, wherein said BRAF mutant sequence at a first position in a BRAF nucleic acid sequence comprises a T1799A mutation in BRAF exon 15.

14. The method of claim 9, wherein said second primer capable of annealing specifically at a second position in a BRAF nucleic acid sequence is SEQ ID NO: 4 or SEQ ID NO: 5.

15. The method of claim 9, wherein said method further comprises a preliminary amplification reaction of said DNA sequences of said sample performed prior to the amplification reaction of step (b), and wherein said preliminary amplification reaction comprises first and second primers capable of annealing specifically to a BRAF DNA sequence, wherein said first and second primers anneal to different strands of double stranded BRAF DNA sequence; and said preliminary amplification reaction produces a BRAF amplification product capable of amplification using said first and second primers of step (b).

16. The method of claim 9, wherein at least one of said first or second primers is fluorescently labeled and amplification products produced by said amplification reaction are fluorescently labeled.

17. A primer comprising the nucleic acid sequence of SEQ ID NO: 6.

18. A primer according to claim 17, wherein said primer is fluorescently labeled.

19. A composition comprising at least one BRAF mutant specific primer and a biologically compatible salt solution, wherein said BRAF mutant specific primer is the primer of claim 17.

20. A method for detecting BRAF mutant status in a subject, said method comprising:
   (a) isolating a sample from said subject, wherein said sample is a tumor sample or a blood sample and comprises DNA sequences;
   (b) performing an amplification reaction of said DNA sequences of said sample, wherein said amplification reaction comprises a first primer capable of annealing specifically to a BRAF mutant sequence at a first position in a BRAF DNA sequence, wherein said first primer is SEQ ID NO: 6 and a second primer capable of annealing specifically at a second position in a BRAF DNA sequence, wherein said second primer is SEQ ID NO: 4 or SEQ ID NO: 5 wherein said amplification reaction is capable of producing a BRAF mutant specific amplification product when said DNA sequences of said sample comprise a BRAF DNA sequence comprising a mutant sequence at said first position of said BRAF DNA sequence; and
   (c) visualizing amplification products produced by said amplification reaction, wherein detection of a BRAF mutant specific amplification product indicates that a BRAF mutant allele is present in said subject.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
agatttctct gtagctagac caaaa                                25

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
atcgagattt ctctgtagct                                      20

<210> SEQ ID NO 3
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 3
agctacagag aaatctcgat ggag                                 24

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 4
tcataatgct tgctctgata gga                                  23

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
ggccaaaaat ttaatcagtg ga                                   22

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
ggtgattttg gtctagctac ata                                  23

<210> SEQ ID NO 7
<211> LENGTH: 21

<212> TYPE: DNA
<213> ORGANISM: Artificial Sequence
<220> FEATURE:
<223> OTHER INFORMATION: Synthetic Oligonucleotide

<400> SEQUENCE: 7
acccactcca tcgagattta t                                          21

<210> SEQ ID NO 8
<211> LENGTH: 360
<212> TYPE: DNA
<213> ORGANISM: Homo sapiens
<220> FEATURE:
<223> OTHER INFORMATION: Synthetic Oligonucleotide

<400> SEQUENCE: 8 tttttattc ttgtgactaa aaacacttat gacccttgat acttttatga tatcaactct    60
ggaagttact gaaagatcat tgagtcgtcg tagagtcccg gtttttaaat tagtcaccttt  120 tttatcggag ttaagaatgg taggtgtttt acctaggtct gttgacaagt ttgactaccc   180
tgggtgaggt agctctaaag tgacatcgat ctggttttag tggataaaaa tgacactcca   240
gaagtacttc tttatataga ctccacatca ttcatttcct tttgtcatct agagtaaaag   300
gatagtctcg ttcgtaatac ttctcaaatc cattctctag attaaagata ttaagacatt   360

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
caaactgatg ggacccactc                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
accatccaca aaatggatcc                                            20

<210> SEQ ID NO 11
<211> LENGTH: 360
<212> TYPE: DNA
<213> ORGANISM: Homo sapiens

<400> SEQUENCE: 11
aatgtcttaa tatctttaat ctagagaatg gatttgagaa gtattacgaa cgagactatc    60
cttttactct agatgacaaa aggaaatgaa tgatgtggag tctatataaa gaagtacttc   120
tggagtgtca ttttatcca ctaaaaccag atcgatgtca ctttagagct acctcaccca    180
gggtagtcaa acttgtcaac agacctaggt aaaacaccta ccattcttaa ctccgataaa   240
aaggtgacta atttaaaaac cgggactcta cgacgactca atgatctttc agtaacttcc   300
agagttgata tcataaaagt atcaagggtc ataagtgttt ttagtcacaa gaataaaaaa   360